United States Patent
Numata et al.

[11] Patent Number: 4,782,094
[45] Date of Patent: Nov. 1, 1988

[54] DIFLUOROBROMOMETHOXYPHENYL DERIVATIVE AND MITICIDE COMPRISING SAID DERIVATIVE AS ACTIVE INGREDIENT

[75] Inventors: Satoshi Numata, Yokohama; Kouji Kitajima, Mobara; Kenji Kodaka, Yokohama; Yukiharu Fukushi, Yokohama; Shiroh Shiraishi, Yokohama; Masahiko Nakamura, Yokohama; Masayuki Ooka, Yokohama, all of Japan

[73] Assignee: Mitsui Toatsu Chemicals, Inc., Tokyo, Japan

[21] Appl. No.: 24,462

[22] Filed: Mar. 11, 1987

[30] Foreign Application Priority Data

Mar. 14, 1986 [JP] Japan .................. 61-45967
Mar. 18, 1986 [JP] Japan .................. 61-58406
Mar. 18, 1986 [JP] Japan .................. 61-58407

[51] Int. Cl.⁴ .................... A01N 43/30; A01N 31/14; C07C 43/267
[52] U.S. Cl. ........................ 514/721; 568/637
[58] Field of Search .................... 568/637; 514/721

[56] References Cited

U.S. PATENT DOCUMENTS 4,599,362  7/1986  Nakatani et al. .................. 568/637
4,661,501  4/1987  Nakatani et al. .................. 568/637

FOREIGN PATENT DOCUMENTS 52202  3/1983  Japan .

Primary Examiner—Howard T. Mars
Attorney, Agent, or Firm—Fisher, Christen & Sabol

[57] ABSTRACT

A difluorobromomethyoxyphenyl derivative of the general formula

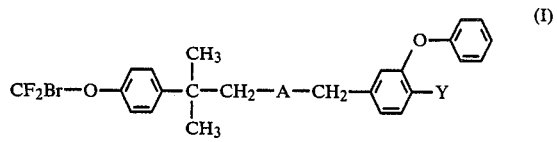

wherein A represents an oxygen atom or a methylene group, and Y represents a hydrogen or fluorine atom. A miticide comprising the above derivative as an active ingredient is also provided.

3 Claims, No Drawings

DIFLUOROBROMOMETHOXYPHENYL DERIVATIVE AND MITICIDE COMPRISING SAID DERIVATIVE AS ACTIVE INGREDIENT

This invention relates to a difluorobromomethoxyphenyl derivative represented by the general formula (I)

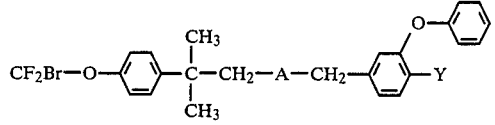

wherein A represents an oxygen atom or a methylene group, and Y represents a hydrogen or fluorine atom, and a miticide comprising the above derivative as an active ingredient.

Compounds of general formula (I) provided by this invention are useful in various industrial fields, and particularly in an agricultural field as agricultural chemicals (an insecticide and a miticide, particularly the latter).

Many compounds having the same skeleton as the compounds of this invention have been known. For example, French Laid-Open Patent Publication No. 2481695 and U.K. Laid-Open Patent Publication No. 2085006 disclose 2-aryl-2-methylpropyl ether derivatives. French Laid-Open Patent Publication No. 2527203 discloses aromatic alkane derivatives.

Among compounds known in the prior art, those of the following general formula (II) are closest to the compounds of the present invention.

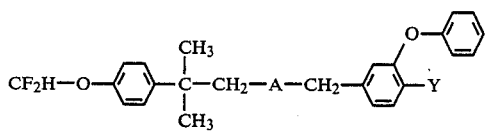

In the formula, A represents an oxygen atom or a methylene group, and Y represents a hydrogen or fluorine atom.

All of the above known compounds have insecticidal and miticidal activities, and are effective against agriculturally and horticulturally important insect pests including mites, such as diamondback moth, green rice leafhopper, small brown planthopper and two-spotted spider mite. But their effects on mites are not entirely sufficient.

Organochlorine compounds such as kelthane, organophosphorus compounds such as TEPP and phosalone, and various other compounds such as Galecron, amitraz and Plictran have been used for controlling mites. In recent years, mites having reduced sensitivity to these chemicals have come into being, and it has become difficult to control these mites by the existing chemicals. It is desired therefore to develop a new type of acaricides different from conventional acaricides.

It is an object of this invention to provide compounds which have a new type of structure and high acaricidal activity against mites resistant to the existing chemicals in order to solve the above problem of the prior art.

The present inventors have made extensive investigations in order to obtain compounds having better insecticidal and miticidal activities, especially better miticidal activity, than the aforesaid known compounds. These investigations have led to the discovery that compounds represented by the following general formula (I)

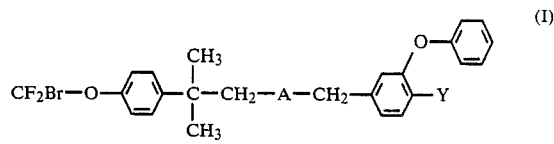

wherein A and Y are as defined above, have markedly improved miticidal activity. The present invention is based on this discovery.

A compound of general formula (I) in which A is an oxygen atom [compound of formula (Ia)] can be easily produced from a compound of formula (III) by the following method.

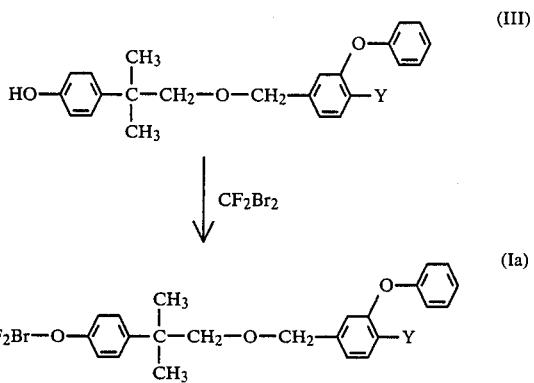

(In the above scheme, Y is as defined above.)

Specifically, a phenol derivative of general formula (III) is reacted with dibromodifluoromethane in a polar solvent such as dimethylformamide (DMF) or 1,3-dimethyl-2-imidazolidinone (DMI) in the presence of a base such as sodium hydride or potassium t-butoxide to give the compound of formula (Ia) [see Tetrahedron Letters, 1981, 323–326].

Alternatively, the compound (Ia) can be easily produced from a compound of formula (IV) and a compound of formula (V) by the following method.

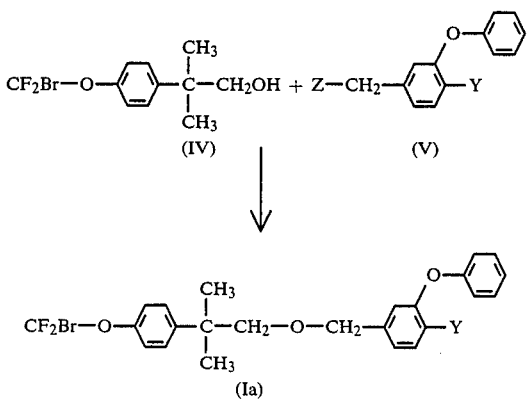

(In the above scheme Y is as defined above, and Z represents a halogen atom.)

Specifically, the compound (Ia) can be synthesized from a 2-aryl-2-methylpropyl alcohol of formula (IV) and a benzyl halide of formula (V) by ordinary etherification. The 2-aryl-2-methylpropyl alcohol of general formula (IV) is not described in the literature, and has been discovered for the first time by the present inventors.

A compound of general formula (I) in which A is a methylene group [compound of formula (Ib)] can be easily produced from a compound of general formula (VI) by the following method.

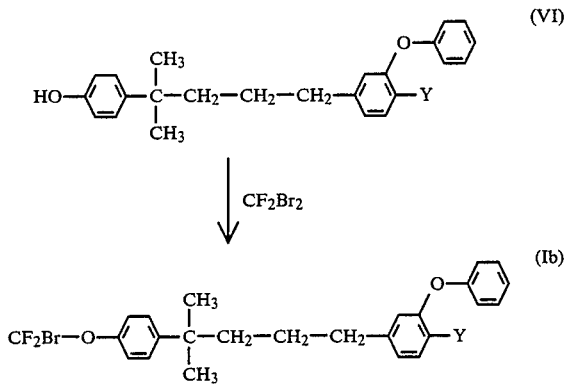

(In the above scheme Y is as defined above.)

In this method, the compound (Ib) can be synthesized under quite the same conditions as in the synthesis of the compound (Ia) from the compound (III). The compounds of general formula (I) provided by this invention have very good miticidal activity on mites of the genus Tetranychus, such as carmine spider mite, Kanzawa spider mite and two-spotted spider mite and mites of the genus Panonychus such as citrus red mite and fruit-tree red spider mite, which are parasitic on fruit trees, vegetables and flowers.

The compounds of the invention are also effective against a variety of insect pests including sanitary insect pests such as fly, mosquito and cockroach; agricultural insect pests, for example hemipterous pests such as small brown planthopper, brown planthopper, whitebacked planthopper, westwood-greenhouse whitefly and green peach aphid, lepidpterous pests such as apple leafminer, diamondback moth, armyworm, cabbage armyworm, tobacco cutworm and common cabbageworm and coleopterous pests such as rice leaf beetle and rice plant weevil; and household insect pests such as termite and bark beetle.

In actual application, the compounds of this invention may be used singly, but for easy application as a controlling agent, it is the general practice to use them in admixture with carriers. Formulating the compounds of this invention requires no special conditions, and they may be prepared into any desired formulations such as emulsifiable concentrates, wettable powders, dusts, granules, microgranules, oil solutions, aerosols and poison baits in accordance with general agricultural chemicals by methods well known to the art. These formulations may be applied according to the purposes for which they are used.

The term "carriers", as used herein, means synthetic or natural inorganic or organic substances which aid in the arrival of the active compounds at the site to be treated, and are mixed with the active compounds to permit their easy storage, transportation and handling.

Suitable solid carriers include, for example, clays such as montmorillonite and kaolinite, inorganic substances such as diatomaceous earth, white terra alba, talc, vermiculite, gypsum, calcium carbonate, silica gel and ammonium sulfate, organic substances derived from plants such as soybean meal, sawdust and wheat flour, and urea.

Suitable liquid carriers include, for example, aromatic hydrocarbons such as toluene, xylene and cumene, paraffinic hydrocarbons such as kerosene and mineral oils, halogenated hydrocarbons such as chloroform and dichloroethane, ketones such as acetone and methyl ethyl ketone, ethers such as dioxane and tetrahydrofuran, alcohols such as methanol, ethanol, propanol and ethylene glycol, dimethylformamide, dimethyl sulfoxide, and water.

In order to enhance the efficacy of the compounds of this invention, various adjuvants may be used singly or in combination according to the types of the formulations, the situation of application, and the purposes for which the adjuvants are applied.

For the purpose of emulsification, dispersion, spreading, wetting, bonding and stabilization, there may be used, for example, water-soluble bases such as lignosulfonic acid salts, nonionic surface-active agents such as alkylbenzenesulfonic acid salts and alkylsulfuric acid esters, lubricants such as calcium stearate and waxes, stabilizers such as isopropyl hydrogen phosphate, methyl cellulose, carboxymethyl cellulose, casein and gum arabic.

Higher miticidal activity may be obtained by using a mixture of two or more of the compounds of the invention as an active ingredient. Furthermore, multipurpose compositions having higher efficacy may be produced by mixing the compounds of the invention with other bioactive substances, and synergistic effects can be expected. Examples of the other bioactive substances include pyrethrum extract and synthetic pyrethroids and isomers thereof, such as allethrin, N-(chrysanthemoylmethyl)-3,4,5,6-tetrahydrophthalimide, 5-benzyl-3-furylmethyl chrysanthemate, 3-phenoxybenzyl chrysanthemate, 5-propargylfurfuryl chrysanthemate, known cyclopropanecarboxylates (e.g., 3-phenoxybenzyl 2,2-dimethyl-3-(2,2-dichlorovinyl)-cyclopropane-1-carboxylate, 3-phenoxy-alphacyanobenzyl 2,2-dimethyl-3-(2,2-dichlorovinyl)-cyclopropane-1-carboxylate and 3-phenoxy-alpha-cyanobenzyl 2,2-dimethyl-3-(2,2-dibromovinyl)-cyclopropane-1-carboxylate) and 3-phenoxy-alpha-cyanobenzyl alpha-isopropyl-4-chlorophenylacetate; organophosphorus insecticides such as O,O-diethyl-O-(3-oxo-2-phenyl-2H-pyridazin-6-yl)phosphorothioate (Ofunack, a registered trademark of Mitsui Toatsu Chemicals, Inc.), O,O-dimethyl-O-(2,2-dichlorovinyl)phosphate (DDVP), O,O-dimethyl-O-(3-methyl-4-nitrophenyl)phosphorothioate, diazinon, O,O-dimethyl-O-4-cyanophenylphosphorothioate, O,O-dimethyl-S-alpha-(ethoxycarbonyl) benzyl]phosphorodithioate, 2-methoxy-4H-1,3,2-benzodioxaphospholine-2-sulfide and O-ethyl-O-4-cyanophenylphosphonothioate; carbamate insecticides such as 1-naphthyl N-methylcarbamate (NAC), m-tolyl N-methylcarbamate (MTMC), 2-dimethylamino-5,6-dimethylpyrimidin-4-yl dimethylcarbamate (pirimor), 3,4-dimethylphenyl N-methylcarbamate and 2-isopropoxyphenyl N-methylcarbamate; aryl propyl ether insecticides such as 3-phenoxybenzyl 2-(4-chlorophenyl)-2-methylpropyl ether, 3-phenoxy-4-fluorobenzyl 2-(4-chlorophenyl)-2-methylpropyl ether, 3-phenoxybenzyl 2-(4-ethoxyphenyl)-2-methylpropyl ether and 3-phenoxy-4-fluorobenzyl 2-(4-ethoxyphenyl)-2-methylpropyl ether; aromatic alkane-type insecticides such as 1-(3-phenoxyphenyl)-4-(4-chlorophenyl)-4-methylpentane, 1-(3-phenoxy-4-fluorophenyl)-4-(4-chlorophenyl)-4-methylpenane, 1-(3-phenoxyphenyl)-4-(4-ethoxyphenyl)-4-methylpentane and 1-(3-phenoxy-4-fluorophenyl)-4-(4-ethoxyphenyl)-4-methylpentane; other insecticides; other miticides; fungicides, nematocides; herbicides; plant growth regulating agents; fertilizers; BT agents; insect hormones; and other agricultural chemicals.

The compounds of this invention are stable to light, heat, oxidation, etc. But as required, compositions having more stabilized effects may be obtained by adding suitable amounts of antioxidants and ultraviolet absorbers, for example phenol derivatives such as BHT (2,6-di-t-butyl-4-methylphenol) and BHA (butylhydroxyanisole), bisphenol derivatives, arylamines such as phenyl-alpha-naphthylamine, phenyl-beta-naphthylamine and a condensation product between phenetidine and acetone, and benzophenone compounds as stabilizers.

The miticide of this invention comprises 0.0001 to 95% by weight, preferably 0.001 to 50% by weight, of the compound of this invention. In application, the miticide of this invention is desirably used in a concentration, calculated as the active ingredient, of generally 0.01 to 5,000 ppm, preferably 0.1 to 1,000 ppm. The rate of application of the miticide, as the active ingredient, is generally 300 to 1 g/10a.

The compounds of general formula (I) provided by this invention are shown in Table 1.

TABLE 1

$$CF_2Br-O-\underset{}{\bigcirc}-\underset{\underset{CH_3}{|}}{\overset{\overset{CH_3}{|}}{C}}-CH_2-A-CH_2-\underset{}{\bigcirc}-Y \quad (I)$$

with $O-\bigcirc$ substituent

| Compound No. | A | Y | $n_D^{20}$ |
|---|---|---|---|
| 1 | O | H | 1.5545 |
| 2 | O | F | 1.5440 |
| 3 | CH$_2$ | H | 1.5482 |
| 4 | CH$_2$ | F | 1.5480 |

The following Referential Examples, Synthesis Examples, Formulation Examples and Test Examples illustrate the present invention in greater detail.

REFERENTIAL EXAMPLE 1

Synthesis of 3-phenoxybenzyl 2-(4-hydroxyphenyl)-2-methylpropyl ether (1) One hundred grams of 3-phenoxybenzyl 2-(3-chloro-4-ethoxyphenyl)-2-methylpropyl ether and 25 g of potassium hydroxide were added to 300 ml of 1,3-dimethyl-2-imidazolidinone (to be abbreviated as DMI hereinafter), and the mixture was stirred at 150° C. for hours. The reaction mixture was cooled to room temperature, poured into water, acidified with a concentrated hydrochloric acid, and extracted with benzene. The benzene solution was washed with water, and dried. Benzene was evaporated under reduced pressure. The resulting oily residue was purified by column chromatography (silica gel; eluent: benzene) to give 45.6 g 3-phenoxybenzyl 2-(3-chloro-4-hydroxyphenyl)-2-methylpropyl ether having a melting point of 68° to 69° C.

(2) The 3-phenoxybenzyl 2-(3-chloro-4-hydroxyphenyl)-2-methylpropyl ether (20.0 g) obtained in (1) above, 2.67 g of 95% sodium hydroxide and 1.0 g of 5% Pd-C (containing water) were added to 100 ml of 80% methanol, and the mixture was stirred at a temperature of 100° C. under a hydrogen pressure of 20 to 30 kg/cm²G for 6 hours. After cooling, the catalyst was removed from the reaction mixture by filtration and fully washed with benzene. The solvent was evaporated under reduced pressure. Dilute hydrochloric acid was added to the residue, and the mixture was extracted with benzene. The benzene solution was washed with water and dried. Benzene was evaporated under reduced pressure to give 18.2 g of the desired 3-phenoxybenzy 2-(4-hydroxyphenyl)-2-methylpropyl ether having a melting point of 69.2° to 70.0° C.

$\delta_{TMS}^{CDCl_3}$ (ppm): 1.29 (6H, s), 3.36 (2H, s), 4.38 (2H, s), 5.07 (1H, s), 6.6–7.4 (13H, m).

| Elemental analysis for $C_{23}H_{24}O_3$: | | |
|---|---|---|
| | C | H |
| Calculated (%): | 79.28 | 6.94 |
| Found (%): | 79.41 | 6.87 |

REFERENTIAL EXAMPLE 2

Synthesis of 1-(3-phenoxyphenyl)-4-(4-hydroxyphenyl)-4-methylpentane

A mixture of 5.0 g of 1-(3-phenoxyphenyl)-4-(4-methoxyphenyl)-4-methylpentane, 30 ml of 47% hydrobromic acid and 30 ml of acetic acid was refluxed for 8 hours. The reaction mixture was cooled to room temperature, poured into water, and extracted with benzene. The benzene solution was washed with water and dried, and benzene was evaporated under reduced pressure. The resulting oily product was purified by column chromatography (silica gel; eluent: benzene) to give 4.2 g of 1-(3-phenoxyphenyl)-4-(4-hydroxyphenyl)-4-methylpentane.

$n_D^{19.4}$: 1.5870

$\nu_{max}^{neat}$ (cm$^{-1}$): 3400, 1610, 1515, 1485, 1440, 1240, 1210, 825, 755, 690, 675.

$\delta_{TMS}^{CCl_4}$ (ppm): 1.00–1.68 (4H, m), 1.20 (6H, s), 2.43 (2H, t), 5.52 (1H, broad s), 6.56–7.38 (13H, m).

REFERENTIAL EXAMPLE 3

Synthesis of 1-(3-phenoxy-4-fluorophenyl)-4-(4-hydroxyphenyl)-4-methylpentane 5.0 g of 1-(3-phenoxy-4-fluorophenyl)-4-(4-methoxyphenyl)-4-methylpentane was treated as in Referential Example 2 to give 3.0 g of 1-(3-phenoxy-4-fluorophenyl)-4-(4-hydroxyphenyl)-4-methylpentane.

$n_D^{19.9}$ : 1.5760

$\nu_{max}^{neat}$ (cm$^{-1}$): 3360, 1620, 1600, 1520, 1435, 1285, 1220, 1130, 840, 760, 700.

$\delta_{TMS}^{CCl_4}$ (ppm): 1.02–1.67 (4H, m), 1.21 (6H, s), 2.39 (2H, t), 5.24 (1H, broad s), 6.52–7.35 (12H, m).

REFERENTIAL EXAMPLE 4

Synthesis of 3-phenoxy-4-fluorobenzyl 2-(4-hydroxyphenyl)-2-methylpropyl ether (1) 5.0 g of 3-phenoxy-4-fluorobenzyl 2-(3-chloro-4-ethoxyphenyl)-2-methylpropyl ether was treated as in Referential Example 1-(1) to give 2.8 g of 3-phenoxy-4-fluorobenzyl 2-(3-chloro-4-hydroxyphenyl)-2-methylpropyl ether.

(2) The 3-phenoxy-4-fluorobenzyl 2-(3-chloro-4-hydroxyphenyl)-2-methylpropyl ether (2.8 g) obtained in (1) above was treated as in Referential Example 1-(2) to give 2.5 g of the desired 3-phenoxy-4-fluorobenzyl 2-(4-hydroxyphenyl)-2-methylpropyl ether.

$\delta_{TMS}^{CCl4}$ (ppm) 1.31 (6H, s), 3.35 (2H, s), 4.40 (2H, s), 6.8–7.5 (11H, m).

| Elemental analysis for $C_{23}H_{23}FO_3$: | | | |
|---|---|---|---|
| | C | H | F |
| Calculated (%): | 75.39 | 6.33 | 5.18 |
| Found (%): | 75.44 | 6.28 | 5.15 |

SYNTHESIS EXAMPLE 1

Synthesis of 3-phenoxybenzyl 2-(4-difluorobromomethoxyphenyl)-2-methylpropyl ether (compound No. 1)

A solution of 21.6 g of 3-phenoxybenzyl 2-(4-hydroxyphenyl)-2-methylpropyl ether and 13.9 g of potassium t-butoxide in 120 ml of DMI was added dropwise to a mixture of 80 g of dibromodifluoromethane and 50 ml of DMI with stirring for 30 minutes at 50° to 60° C., and the mixture was maintained at this temperature for 3 hours. The reaction mixture was poured into water and extracted with toluene. The toluene solution was washed with dilute hydrochloric acid and water in this order, and dried. Toluene was evaporated under reduced pressure to give 29.4 g of an oily residue. The oily residue was purified by column chromatography [silica gel: 600 g; eluent: toluene/hexane (1:1)] to give 12.4 g of the desired 3-phenoxybenzyl 2-(4-difluorobromomethoxyphenyl)-2-methylpropyl ether.

$n_D^{20}$: 1.5545

$\nu_{max}^{neat}$ (cm$^{-1}$): 1260, 1230, 1205, 1150, 1110, 1020.

$\delta_{TMS}^{CCl4}$ (ppm): 1.33 (6H, s), 3.37 (2H, s), 4.39 (2H, s), 6.78–7.4 (13H, m).

Mass analysis (EI Mass): m/z 264, 477 (M+).

SYNTHESIS EXAMPLE 2

Synthesis of 3-phenoxy-4-fluorobenzyl 2-(4-difluorobromomethoxyphenyl)-2-methylpropyl ether (compound No. 2)

(1) 3.0 g of 3-phenoxybenzyl 2-(4-difluorobromomethoxyphenyl)-2-methylpropyl ether was dissolved in 50 ml of chloroform, and then 1.7 g of trimethylsilyl iodide was added at 0° C. After the addition, the mixture was stirred at room temperature for 3.5 hours. Methanol (10 ml) was added, and the reaction mixture was washed with sodium hydrogen sulfite, sodium hydrogen carbonate and water in this order, and dried. Chloroform was evaporated, and the oily product was purified by column chromatography [silica gel; eluent: hexane/ethyl acetate (8:1)] to give 1.2 g of 2-(4-difluorobromomethoxyphenyl)-2-methylpropyl alcohol.

Mass analysis (EI Mass): m/z 264, 277, 295 (M+)

(2) 1.7 g of 2-(4-difluorobromomethoxyphenyl)-2-methylpropyl alcohol obtained as in (1) above, 1.6 g of 3-phenoxy-4-fluorobenzyl bromide and 0.5 g of triethylbenzyl ammoniumbromide were added to 20 ml of a 50% aqueous solution of NaOH, and the mixture was stirred at room temperature for 3 hours. Water was added to the reaction mixture, and the mixture was extracted with benzene. The benzene solution was washed with dilute hydrochloric acid and water in this order, and dried. Benzene was evaporated under reduced pressure. The resulting oily product was purified by column chromatography [silica gel; eluent: toluene/hexane (1:4)] to give 1.5 g of 3-phenoxy-4-fluorobenzyl 2-(4-difluorobromomethoxyphenyl)-2-methylpropyl ether.

$n_D^{20}$: 1.5440

Mass analysis (EI Mass): m/z 264, 495 (M+)

SYNTHESIS EXAMPLE 3

Synthesis of 3-phenoxy-4-fluorobenzyl 2-(4-difluorobromomethoxyphenyl)-2-methylpropyl ether (compound No. 2)

Synthesis Example 1 was repeated except that 3.5 g of 3-phenoxy-4-fluorobenzyl 2-(4-hydroxyphenyl)-2-methylpropyl ether was used instead of 21.6 g of 3-phenoxybenzyl 2-(4-hydroxyphenyl)-2-methylpropyl ether. There was obtained 1.7 g of the desired 3-phenoxy-4-fluorobenzyl 2-(4-difluorobromomethoxyphenyl)-2-methylpropyl ether.

$n_D^\circ$: 1.5440

Mass spectrum (EI Mass): m/z 264, 495 (M+)

SYNTHESIS EXAMPLE 4

Synthesis of 1-(3-phenoxyphenyl)-4-(4-difluorobromomethoxyphenyl)-4-methylpentane (compound No. 3)

A solution of 20.0 g of 1-(3-phenoxyphenyl)-4-(4-hydroxyphenyl)-4-methylpentane and 13.0 g of potassium t-butoxide in 120 ml of DMI was added dropwise to a mixture of 80 g of dibromodifluoromethane and 50 ml of DMI with stirring at 50° C. for 30 minutes. The mixture was maintained at this temperature for 3 hours, poured into water, and extracted with toluene. The toluene solution was washed with dilute hydrochloric acid and water in this order, and dried. Toluene was evaporated, and the resulting oily product was purified by column chromatography [silica gel; eluent: toluene/hexane (1:2)] to give 12.6 g of the desired 1-(3-phenoxyphenyl)-4-(4-difluorobromomethoxyphenyl)-4-methylpentane.

$n_D^{20}$: 1.5482

$\nu_{max}^{neat}$ (cm$^{-1}$): 1580, 1480, 1240, 1205, 1095, 1140, 1000.

$\delta_{TMS}^{CCl4}$ (ppm): 1.1–1.8 (4H, m), 1.28 (6H, s), 2.47 (2H, t, J=6.8 Hz), 6.6–7.4 (13H, m).

SYNTHESIS EXAMPLE 5

Synthesis of 1-(3-phenoxy-4-fluorophenyl)-4-(4-difluorobromomethoxyphenyl)-4-methylpentane (compound No. 4)

Synthesis Example 4 was repeated except that 20 g of 1-(3-phenoxy-4-fluorophenyl)-4-(4-hydroxyphenyl)-4-methylpentane was used instead of 20 g of 1-(3-phenoxyphenyl)-4-(4-hydroxyphenyl)-4-methylpentane. There was obtained 13.5 g of the desired 1-(3-phenoxy-4- fluorophenyl)-4-(4-difluorobromomethoxyphenyl)-4-methylpentane.

$n_D^{20}$: 1.5480

$\nu_{max}^{neat}$ (cm$^{-1}$): 1580, 1505, 1485, 1280, 1210, 1160, 1140, 1000.

$\delta_{TMS}^{CCl_4}$ (ppm): 1.1–1.8 (4H, m), 1.30 (6H, s), 2.45 (2H, t, J=6.9 Hz), 6.6–7.4 (12H, m).

The following Formulation Examples specifically illustrate the composition of this invention.

FORMULATION EXAMPLE 1

Twenty parts of the compound of the invention, parts of Sorpol (a surface-active agent made by Toho Chemical Industrial Co., Ltd.) and 70 parts of xylene are uniformly mixed with stirring to give an emulsifiable concentrate.

FORMULATION EXAMPLE 2

Twenty parts of the compound of the invention, parts of sodium alkylnaphthalenesulfonate, 5 parts of sodium lignosulfonate, 5 parts of white carbon, and 68 parts of diatomaceous earth are uniformly mixed with stirring to give a wettable powder.

FORMULATION EXAMPLE 3

Three parts of the compound of the invention is dissolved in acetone, and while the solution is mixed with 97 parts of clay, acetone is evaporated to give a dust.

FORMULATION EXAMPLE 4

Three parts of the compound of the invention, 2 parts of sodium lignosulfonate and 95 parts of bentonite are uniformmly pulverized and mixed, and kneaded together with water. The mixture is granulated and dried to give granules.

FORMULATION EXAMPLE 5

The compound of the invention (0.1 part), 0.5 part of piperonyl butoxide and 99.4 parts of kerosene are uniformly dissolved and mixed to give an oil solution.

FORMULATION EXAMPLE 6

The compound of the invention (0.4 part), 2.0 parts of piperonyl butoxide and 7.6 parts of deodorized kerosene are uniformly dissolved and mixed and filled in an aerosol container. A propelling valve is fitted to it, and then 90 parts of liquefied petroleum gas is filled into the container under pressure to give an aerosol.

FORMULATION EXAMPLE 7

BHT (0.05 part) is added to 0.05 g of the compound of this invention and the mixture is dissolved in a suitable amount of chloroform. The solution is uniformly adsorbed on the surface of asbestos having a size of 2.5 cm × 1.5 cm with a thickness of 0.3 cm to form a heating insecticidal fumigant to be placed on a hot plate.

FORMULATION EXAMPLE 8

One part of the compound of the invention, 5 parts of sugar, 50 parts of wheat bran, 20 parts of rice bran and 24 parts of wheat flour are uniformly mixed, and kneaded together with a suitable amount of water. The mixture is granulated and dried to give a poson bait.

FORMULATION EXAMPLE 9

Ten parts of the compound of the invention, 20 parts of a 10% aqueous solution of polyvinyl alcohol and 5 parts of xylene are uniformly mixed with stirring and 65 parts of water is added. The mixture is again stirred to give a flowable agent.

The following Test Examples specifically illustrate the excellent miticidal activity of the compounds of this invention.

The following compounds (IIa), (IIb), (IIc) and (IId), amitraz, dicofol and phosalone were used as control compounds.

Control compound (IIa)

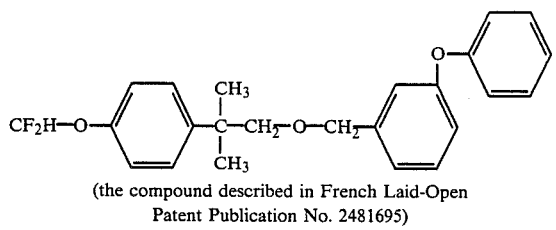

(the compound described in French Laid-Open Patent Publication No. 2481695)

Control compound (IIb)

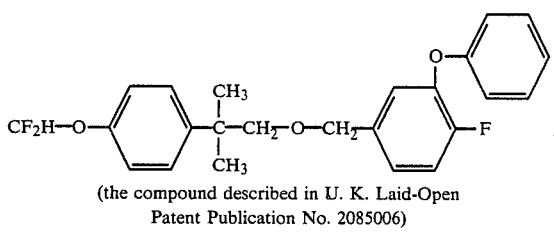

(the compound described in U. K. Laid-Open Patent Publication No. 2085006)

Control compound (IIc)

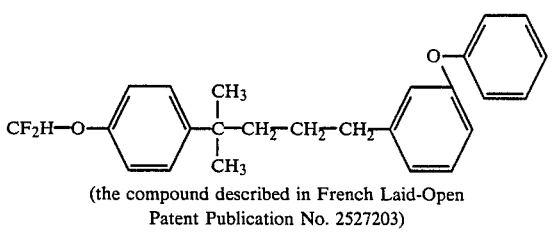

(the compound described in French Laid-Open Patent Publication No. 2527203)

Control compound (IId)

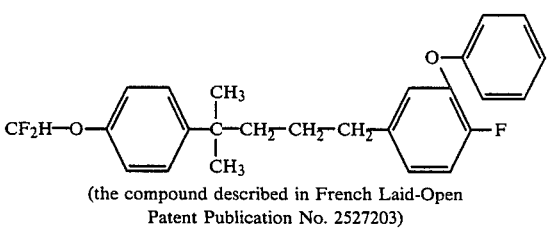

(the compound described in French Laid-Open Patent Publication No. 2527203)

Control compound, amitraz

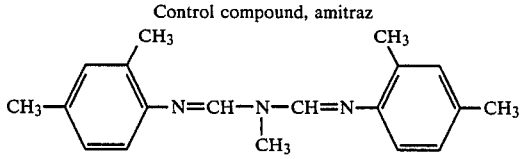

Control compound, dicofol

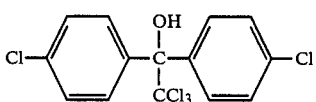

Control compound, phosalone

-continued

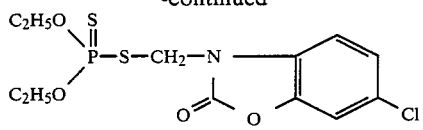

TEST EXAMPLE 1

Effect on two-spotted spider mite (*Tetranychus urticae*)

A square piece, each side measuring about 2 cm, of a kidney bean leaf was placed on water-impregnated adsorbent cotton, and 20 female adults of two-spotted spider mite were set free on it. Twenty-four hours later, 4 ml of a 10 ppm dilution of an emulsifiable concentrate of each of the test compounds prepared as in Formulation Example 1 was applied with a spray-tower, and the resulting set was placed in an incubator at 25° C. Forty-eight hours later, the mortality of the mites was examined, and the results are shown in Table 2. The test was conducted through two replications.

TEST EXAMPLE 2

Effect on two-spotted spider mite (*Tetranychus urticae*)

A square piece, each side measuring about 2 cm, of a kidney bean leaf was placed on wetted adsorbent cotton, and 20 female adults of two-spotted spider mite were set free on it. Twenty-four hours later, 4 ml of a dilution of an emulsifiable concentrate of each of the test compounds prepared as in Formulation Example 1 in the concentrations shown in Table 3 was applied with a spray tower, and the resulting set was placed in an incubator at 25° C. Forty-eight hours later, the mortality of the mites was examined, and the results are shown in Table 3. The test was conducted through three replications.

TEST EXAMPLE 3

Effect on carmine spider mite (*Tetranychus telarius*)

Ten female adults of carmine spider mite were set free on a kidney bean seedling in the two leaf stage grown in a pot having a diameter of 6 cm, and the pot was placed in a greenhouse. Five days later, again 10 female adults of the mite were set free. Ten days after the first release, a 25 ppm dilution of an emulsifiable concentrate of each of the test compounds prepared as in Formulation Example 1 was sprayed at a rate of 20 ml per pot. Seven days and 14 days later, the number of the mites parasitic on the seedling was examined. The test was conducted through 5 replications using 5 pots, and the average value obtained in the five pots was calculated. The results are shown in Table 4.

TEST EXAMPLE 4

Effect on citrus red mite (*Panonychus citri*)

A 10 ppm dilution of an emulsifiable concentrate of each of the test compounds prepared as in Formulation Example 1 was sprayed onto a two-year-old Satsuma orange seedling grown in a pot so that it lightly dripped. The pot was placed in a greenhouse. Twenty days after the spraying of the chemical, five leaves were taken at random from the seedling, and leaf discs having a diameter of about 2 cm were prepared from them. The leaf discs were placed on agar gel, and 10 female adults of citrus red mite were set free on the discs. These discs were placed in an incubator at 25° C. for 48 hours to permit oviposition. The adults were removed, and 10 days later, the number of adults, nymphs and larvae living on the discs was examined. The results are shown in Table 5.

TEST EXAMPLE 5

Effect on resistant strain of two-spotted spider mite

A 30 ppm dilution of a wettable powder of each of the test compounds prepared as in Formulation Example 2 was sprayed onto cucumber seedlings in the 3 to 4 leaf stage at a rate of 30 ml per seedling, and then air-dried. Four leaf discs having a diameter of about 2 cm were prepared arbitrarily from each seedling, and placed on wetted adsorbent cotton. Ten female adults of two-spotted spider mite having resistance to orgaonophosphorus agents and dicofol were set free on the discs, and the resulting set was placed in an incubator at 25° C. Forty-eight hours later, the number of living mites was examined, and the results are shown in Table 6.

TABLE 2

| Test compound No. | Mortality (%) |
|---|---|
| 3 | 100 |
| 4 | 100 |
| Control (IIc) | 15 |
| Control (IId) | 70 |
| Non-treated | 3.3 |

TABLE 3

| | Mortality (%) | |
|---|---|---|
| Test compound No. | 10 ppm | 2 ppm |
| 2 | 100 | 25 |
| Control (IIb) | 47 | 5.0 |
| Non-treated | 3.3 | |

TABLE 4

| | Average number of parasitic mites per 5 seedlings | |
|---|---|---|
| Test compound No. | 7 days later | 14 days later |
| 1 | 0 | 0 |
| 2 | 0 | 0 |
| 3 | 0 | 0 |
| 4 | 0 | 0 |
| Control (IIa) | 36 | 280 |
| Control (IIb) | 20 | 320 |
| Control (IIc) | 41 | 340 |
| Control (IId) | 39 | 265 |
| Non-treated | 452 | (withered) |

TABLE 5

| Test Compound No. | Total number of living mites |
|---|---|
| 1 | 0 |
| 2 | 0 |
| 3 | 0 |
| 4 | 0 |
| Control (IIa) | 104 |
| Control (IIb) | 80 |
| Control (IIc) | 96 |
| Control (IId) | 115 |
| Amitraz | 155 |
| Non-treated | 163 |

TABLE 6

| Test compound No. | Ratio of living mites (%) |
| --- | --- |
| 1 | 0 |
| 2 | 0 |
| 3 | 0 |
| 4 | 0 |
| Control (IIa) | 73 |
| Control (IIb) | 70 |
| Control (IIc) | 65 |
| Control (IId) | 90 |
| Dicofol | 95 |
| Phosalone | 100 |
| Non-treated | 100 |

As is clearly seen from the foregoing description, the difluorobromomethoxyphenyl derivatives of general formula (I) provided by this invention show excellent miticidal activity. Agricultural chemicals containing the difluorobromomethoxyphenyl derivatives of general formula (I) provided by this invention have excellent characteristics as miticides.

What is claimed is:

1. A difluorobromomethoxyphenyl derivative represented by the following general formula (I)

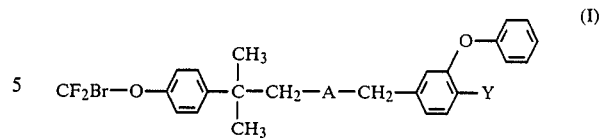

wherein A represents an oxygen atom or a methylene group, and Y represents a hydrogen or fluorine atom.

2. The difluorobromomethoxyphenyl derivative of claim 1 wherein A in general formula (I) represents an oxygen atom.

3. A miticidal composition, comprising a carrier or vehicle and, as an active ingredient, a miticidal effective amount of one or two members selected from the group consisting of the difluorobromomethoxyphenyl derivatives represented by the following formula (I)

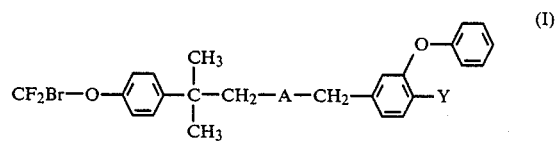

wherein A represents an oxygen atom or a methylene group, and Y represents a hydrogen or fluorine atom.

* * * * *